US010945390B2

(12) United States Patent
Bullock et al.

(10) Patent No.: US 10,945,390 B2
(45) Date of Patent: Mar. 16, 2021

(54) METHOD OF SELECTING CORN EMBRYOS

(71) Applicant: Syngenta Participations AG, Basel (CH)

(72) Inventors: William Paul Bullock, Slater, MN (US); Ulrich Stephan Hannappel, Slater, MN (US); Katie Marie Hunter, Slater, MN (US)

(73) Assignee: Syngenta Participations AG, Basel (CH)

( * ) Notice: Subject to any disclaimer, the term of this patent is extended or adjusted under 35 U.S.C. 154(b) by 424 days.

(21) Appl. No.: 15/743,191

(22) PCT Filed: Jul. 6, 2016

(86) PCT No.: PCT/EP2016/065996
§ 371 (c)(1),
(2) Date: Jan. 9, 2018

(87) PCT Pub. No.: WO2017/005800
PCT Pub. Date: Jan. 12, 2017

(65) Prior Publication Data
US 2019/0116746 A1    Apr. 25, 2019

Related U.S. Application Data

(60) Provisional application No. 62/190,548, filed on Jul. 9, 2015.

(51) Int. Cl.
*A01H 1/04*       (2006.01)
*C12Q 1/6895*    (2018.01)
*C12N 15/10*     (2006.01)

(52) U.S. Cl.
CPC ........... *A01H 1/04* (2013.01); *C12N 15/1003* (2013.01); *C12Q 1/6895* (2013.01); *C12Q 2600/13* (2013.01)

(58) Field of Classification Search
CPC .................................. A01H 1/04; A01H 4/00
See application file for complete search history.

(56) References Cited

U.S. PATENT DOCUMENTS

| 8,980,632 B2 * | 3/2015 | Bullock ............... A01C 1/00 |
| | | 435/420 |
| 2005/0246786 A1 | 11/2005 | Adams et al. |
| 2011/0078819 A1 | 3/2011 | Bullock |

FOREIGN PATENT DOCUMENTS

| WO | 2011019863 A1 | 2/2011 | |
| WO | WO 2011/019863 * | 2/2011 | ............... A01H 4/00 |
| WO | 2014071271 A1 | 5/2014 | |
| WO | 2015104358 A1 | 7/2015 | |
| WO | 2016032589 A1 | 3/2016 | |

OTHER PUBLICATIONS

Wu, M. et al. Molecular Plant Breeding, 2006; vol. 4, No. 3; pp. 381-384. (Year: 2006).*
International Search Report for International Patent Application No. PCT/EP2016/065996 dated Oct. 13, 2016.
Shibin Gao et al., "Development of a seed DNA-based genotyping system for marker-assisted selection in maize" Molecular Breeding, Kluwer Academic Publishers, vol. 22, No. 3, May 22, 2008, pp. 477-494, XP019611846, ISSN: 1572-9788m abstractM pp. 478-481, 485-491, Tables 4-6.
G. Meru et al., "A non-destructive genotyping system from a single seed for marker-assited selection in watermelon" Jan. 1, 2013, XP 055216157.
Salvaor Soler et al., "Use of Embryos Extracted from Individual Cannabis sativa Seeds for Genetic Studies and Forensic Applications" Mar. 1, 2016, XP055303245.

* cited by examiner

*Primary Examiner* — Russell Kallis
(74) *Attorney, Agent, or Firm* — Christopher Leming

(57) ABSTRACT

The present invention relates to a viability-retaining method of selecting corn embryos having a desired trait, said method comprising extracting embryos, removing associated non-embryogenic tissue or DNA from the exterior of the embryo; and extracting DNA directly from the embryo. The invention surprisingly shows that germinating embryos sampled directly for their DNA content are capable of continuing the germination process to form normal seedlings.

14 Claims, 13 Drawing Sheets

Assay 1　　　　Assay 2　　　　Assay 3

METHOD OF SELECTING CORN EMBRYOS

RELATED APPLICATION INFORMATION

Figure 1:
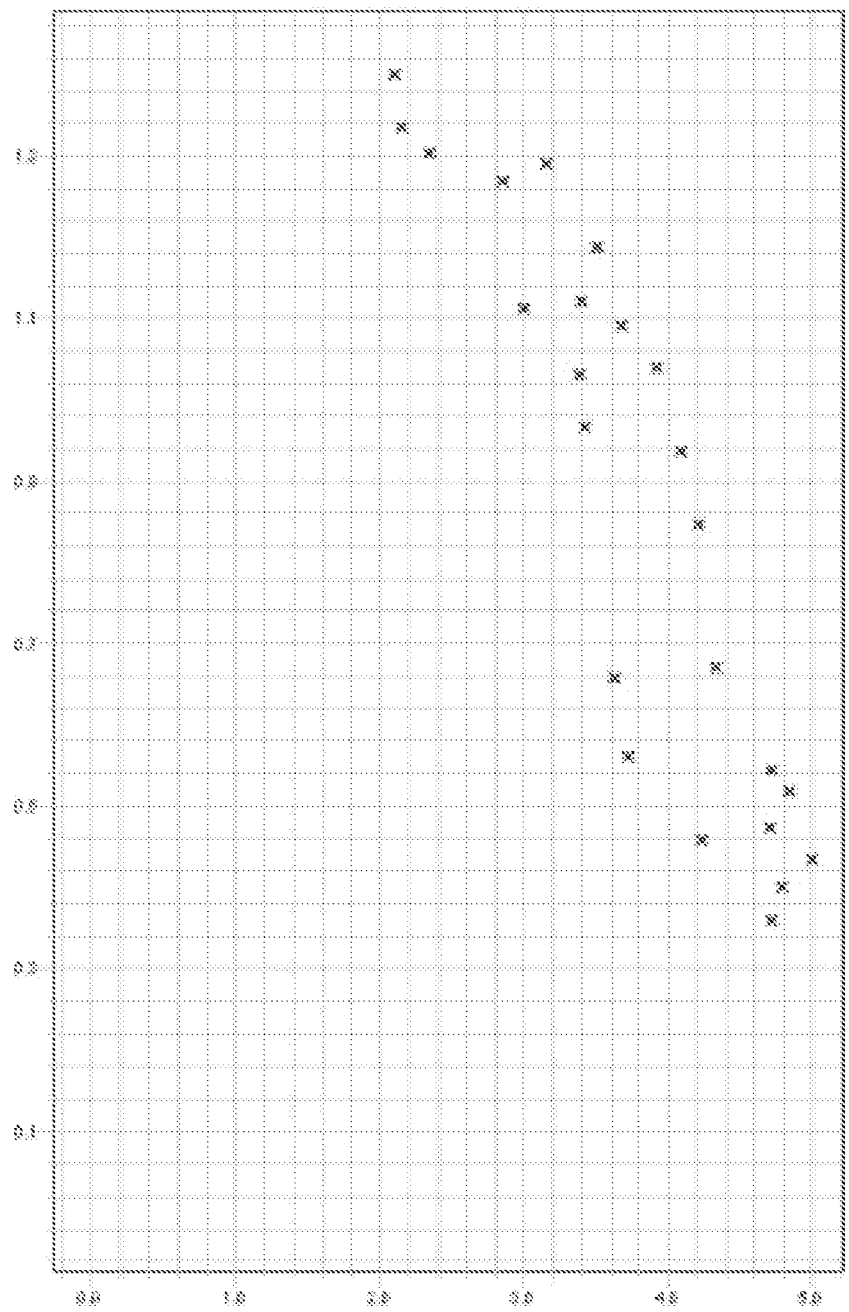

This application is a 371 of International Application No. PCT/EP2016/065996, filed Jul. 6, 2016, which claims priority to U.S. Application No. 62/190,548, filed Jul. 9, 2015, the contents of both of which are hereby incorporated in their entirety by reference herein.

INTRODUCTION

Maize doubled haploidy has become a critical and integral process in plant breeding. In this regard, the ability to make data driven decisions in terms of the selection of desired haploid genotypes early in the DH process and the advancement only of the genetically desired individuals for further processing have together become very important cost and efficiency factors.

It has previously been illustrated that it is possible to isolate DNA directly from a precocious seedling for genotyping purposes. However in this methodology, removal of tissue from the scutellar region is not required. Germination capacity of the immature corn embryo or precocious seedling can be retained post DNA removal by this process.

DESCRIPTION

The direct removal of DNA from an immature corn embryo can be confounded by the presence of unwanted exogenous contaminating paternal DNA. The present invention describes methods to remove this confounding DNA and then directly extract DNA reflecting the maternal genotype of the haploid embryo.

This present invention surprisingly shows that germinating embryos sampled directly for their DNA content are indeed capable of continuing the germination process to form normal seedlings.

The present invention also describes a viability-retaining method of selecting corn embryos having a desired trait, said method comprising:
  a) extracting embryos;
  b) removing associated non-embryogenic tissue or DNA from the exterior of the embryo; and
  c) Extracting DNA directly from the embryo.

In one embodiment, the embryos are corn embryos, preferably immature corn embryos. Typically, the embryos are 15 to 20 days old, preferably 17 days old.

In one embodiment, steps a) and b) are performed simultaneously using a liquid stream of solution. Preferably, the embryos are extracted in sterile conditions.

In one embodiment, the liquid stream of solution is provided via a power washer as described in U.S. Pat. No. 8,980,632.

In one embodiment, step b) comprises performing DNA extraction by contacting the embryos with a cell lysis solution which disrupts cells but does not reduce embryo viability.

In one embodiment, step b) comprises contacting the embryos with a solution comprising nutritional salt before DNA extraction. In one embodiment, said solution further comprises a carbohydrate source.

In one embodiment, step b) comprises contacting the embryos with a soaking solution comprising nutritional salt and optionally a carbohydrate source after DNA extraction.

In one embodiment, step b) comprises contacting the embryos with a solution comprising a nutritional salt and optionally a carbohydrate source before DNA extraction and a soaking solution comprising a nutritional salt and optionally a carbohydrate source after DNA extraction.

In a preferred embodiment, the solution comprising a nutritional salt is MS salt medium.

In a preferred embodiment, the solution comprising a nutritional salt and a carbohydrate source is MS salt plus sucrose liquid medium. In an alternative embodiment, sucrose can be substituted by maltose. The carbohydrate concentration is preferably in range 1 to 5%, preferably 2 to 4%, most preferably 3%.

In a preferred embodiment, the extracted embryos are exposed to light. Typically, the light is 300 to 500 umol PAR light, preferably 400 umol. Typically, the extracted embryos are exposed to light for 12 to 20 hours, preferably 16 hours. Typically, the extracted embryos are kept in the light at 25 to 35 C, preferably 30 C.

In one embodiment, step b) comprises washing the embryos post extraction to remove associated non-embryogenic tissue or DNA.

In one embodiment, the washing step comprises contacting the embryos with a liquid, preferably water.

In one embodiment, the washing step comprises contacting the embryos with a solution comprising a nutritional salt and optionally a carbohydrate source.

In one embodiment, the washing step comprises contacting the embryos with water followed by a solution comprising a nutritional salt and optionally a carbohydrate source.

In one embodiment, the washing step further comprises the use of an abrasive, preferably silica powder. Typically, 4% to 12% (vol) silica powder is used. Preferably, 8% (vol) silica powder is used.

In one embodiment, the washing step comprises shaking, preferably for a duration of 1 to 60 minutes, more preferably 1 to 25 minutes. Typically, a horizontal shaker is used.

In one embodiment, the method comprises the use of sonication.

In one embodiment, the embryos are mechanically opened to further facilitate removal of DNA from ruptured embryonic cells. Typically, the embryos are mechanically opened using a razor blade.

In one embodiment, the contaminants are removed enzymatically. The enzyme may for example be selected from DNASE, BENZONASE, CYANASE or a mixture thereof.

In one embodiment, the contaminant is starch.

In one embodiment the contaminant is non-embryogenic DNA.

In one embodiment the contaminant is non-embryogenic tissue.

In one embodiment the non-embryogenic tissue is degraded via a cell wall degrading enzyme.

In one embodiment oxygenated bleach is used to remove non-embryogenic DNA. In a preferred embodiment, the oxygenated bleach comprises hydrogen peroxide.

In one embodiment, molecular marker analysis is performed using DNA extracted from embryos.

In one embodiment, the DNA is additionally cleaned or concentrated before molecular marker analysis.

In one embodiment, the DNA is cleaned and concentrated via alcohol precipitation.

In one embodiment, the embryo is an immature embryo.

In one embodiment, the method is automated or semi-automated.

For all experiments in examples 1 and 2 post pollination with a haploid inducer, 17 day old immature corn embryos were extracted in a sterile fashion using a spatula and placed onto a filter paper (moistened with Murashige and Skoog salt plus 3% sucrose liquid medium) inside a petri dish. The embryos were then transferred onto another filter paper supplemented with MS liquid medium containing 3% sucrose. The petri dish containing embryos was placed into a growth room such that the embryos were exposed to approximately 16 hours of 400 umol PAR light at 30.5 C.

DNA extraction for all experiments was performed via cell lysis: 24 Embryos were transferred into wells of a 96 well block. To each well a solution of 100 mM TrisHCl pH 9.1 and 0.0025% SDS. The 96 well block was placed on a horizontal shaker, the blocks were slowly agitated for 1 hour. The TrisHCl/SDS solution disrupts scutellar or embryo axis cells releasing the cellular content into the solution. The salt concentration of the soaking solution can be higher or lower. The soaking time can also be shortened or prolonged. Any other chemical which disrupts cells but does not harm the viability of the embryos could be used or any chemical substances which do not harm the viability of the embryos could be added to a cell disrupting solution. After 1 hour the soaking solution was transferred into a new 96 well block.

After DNA extraction, embryos were briefly rinsed with MS buffer containing 3% sucrose. Germination test of treated embryos from example 1 (experiments 1 to 4) was performed in petri dishes containing filter paper soaked with MS buffer containing 3% sucrose. For example 2 (experiments 5 to 8) germination test was performed in solidified medium containing MS buffer and 3% sucrose.

The following experiments describe the effect of different methods on the removal of unwanted paternal DNA.

Embryos were either rinsed post extraction or placed directly onto filter paper without rinsing post extraction. Before DNA extraction, additional methods were applied to remove endosperm tissue and/or non-embryonic DNA.

EXAMPLES

The following examples serve to illustrate various embodiments of the invention but are in no way intended to limit the scope of the invention.

Example 1

Experiments 1-4

Experiment 1: 24 Embryos which had not been rinsed prior to placing them onto filter paper post extraction were pooled and transferred into a 50 ml tube containing 40 ml MS buffer and 3% sucrose. The tube was placed on a horizontal shaker and vigorously shaken for 25 minutes. After 25 minutes the washing solution was poured off and the embryos were briefly rinsed in $H_2O$ for DNA extraction as described above. After DNA extraction embryos were briefly rinsed with MS buffer containing 3% sucrose and placed into petri dished containing filter paper soaked in MS buffer containing 3% sucrose. The germination rate of the treated embryos was comparable to the untreated controls (embryos which were not washed and soaked in cell lysis buffer for DNA extraction).

For molecular marker analysis, the DNA from 24 embryos which was released into the soaking solution was used directly as a template for Taqman PCRs. Modification of the DNA (e.g. additional cleaning steps via alcohol precipitation) could be applied. Direct PCR results are shown in FIG. 1. This image clearly demonstrates the problem: No distinct allelic clusters are formed which is very likely due to the co-extraction of a second (paternal) allele. Washing the embryos before DNA extraction with MS buffer was not sufficient for this tested assay to remove endosperm tissue and/or paternal DNA.

Figure 2:
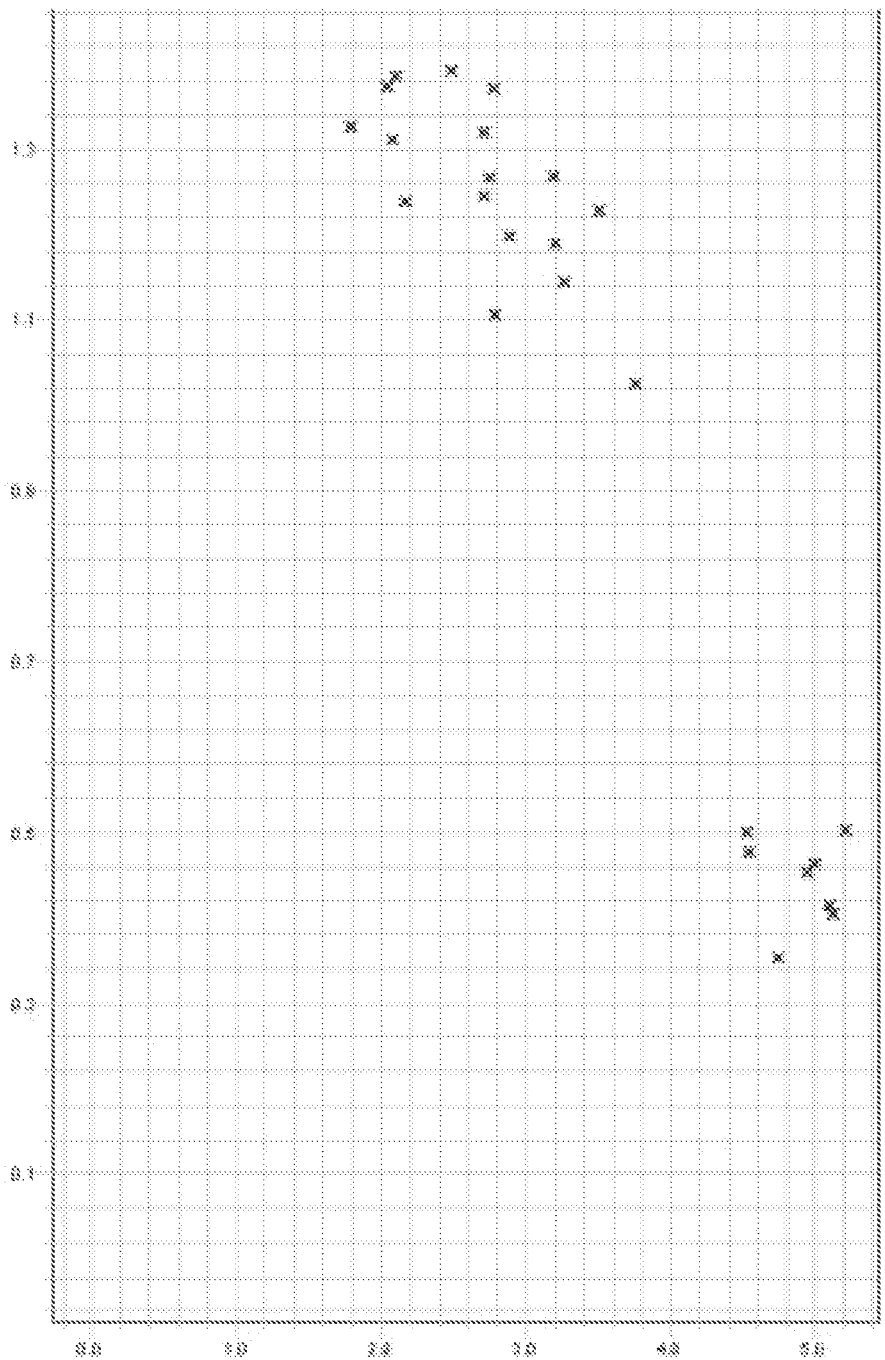

Experiment 2: As in the first experiment, 24 embryos which had not been rinsed prior to placing them onto filter paper post extraction were pooled and transferred into a 50 ml tube containing 40 ml MS buffer and 3% sucrose. To enhance the washing efficiency, 12.5% (vol.) of silica gel powder (Sigma 288594) was added to the washing solution. After 25 minutes the washing solution was poured off and the embryos were briefly rinsed in $H_2O$ for DNA extraction as described. After DNA extraction, embryos were briefly rinsed with MS buffer containing 3% sucrose and placed into petri dished containing filter paper soaked in MS buffer containing 3% sucrose. The germination rate of treated embryos was comparable to that of untreated controls (embryos which were not washed and soaked in cell lysis buffer for DNA extraction). Again the DNA from 24 embryos which was released into the soaking solution was used directly as a template for Taqman PCRs. Results are shown in FIG. 2. Two well separated allelic clusters are formed, a genotypic analysis for this marker is possible. The added silica powder had a positive effect with regard to removing endosperm tissue and/or paternal DNA.

Experiment 3: Post extraction 24 embryos which had been rinsed twice with 25 ml MS buffer before placing them onto filter paper overnight were pooled and transferred into a 50 ml tube containing 40 ml MS buffer and 3% sucrose. The tube was placed on a horizontal shaker and vigorously shaken for 25 minutes. After 25 minutes, the washing solution was poured off and the embryos were briefly rinsed in $H_2O$ for DNA extraction as described above. After DNA extraction embryos were briefly rinsed with MS buffer containing 3% sucrose and placed into petri dished containing filter paper soaked in MS buffer containing 3% sucrose. Germination rate of treated embryos was comparable to untreated controls (embryos which were not washed and soaked in cell lysis buffer for DNA extraction).

Figure 3:
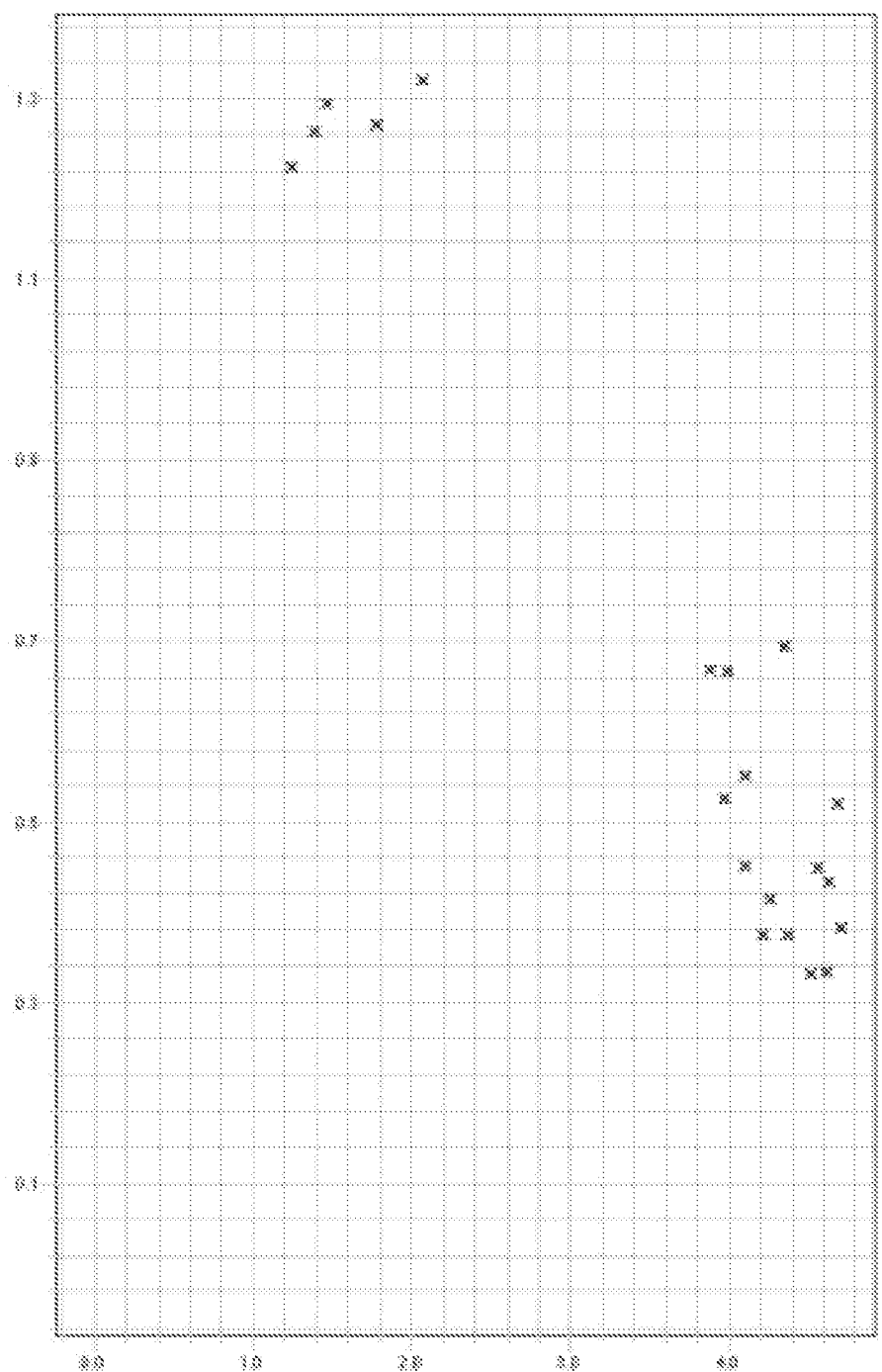

For molecular marker analysis, the DNA from 24 embryos which was released into the soaking solution was used directly as a template for Taqman PCRs. Modification of the DNA (e.g. additional cleaning steps via alcohol precipitation) could be applied. Direct PCR results are shown in FIG. 3.

Experiment 4: Post extraction 24 embryos which had been rinsed twice with 25 ml MS buffer before placing them onto filter paper overnight were pooled and transferred into a 50 ml tube containing 40 ml MS buffer and 3% sucrose. The tube was placed on a horizontal shaker and vigorously shaken for 25 minutes. To enhance the washing efficiency 12.5% (vol.) of silica gel powder (Sigma 288594) was added to the washing solution After 25 minutes the washing solution was poured off and the embryos were briefly rinsed in $H_2O$ for DNA extraction as described above. After DNA extraction embryos were briefly rinsed with MS buffer containing 3% sucrose and placed into petri dished containing filter paper soaked in MS buffer containing 3% sucrose. Germination rate of treated embryos was comparable to untreated controls (embryos which were not washed and soaked in cell lysis buffer for DNA extraction).

Figure 4:
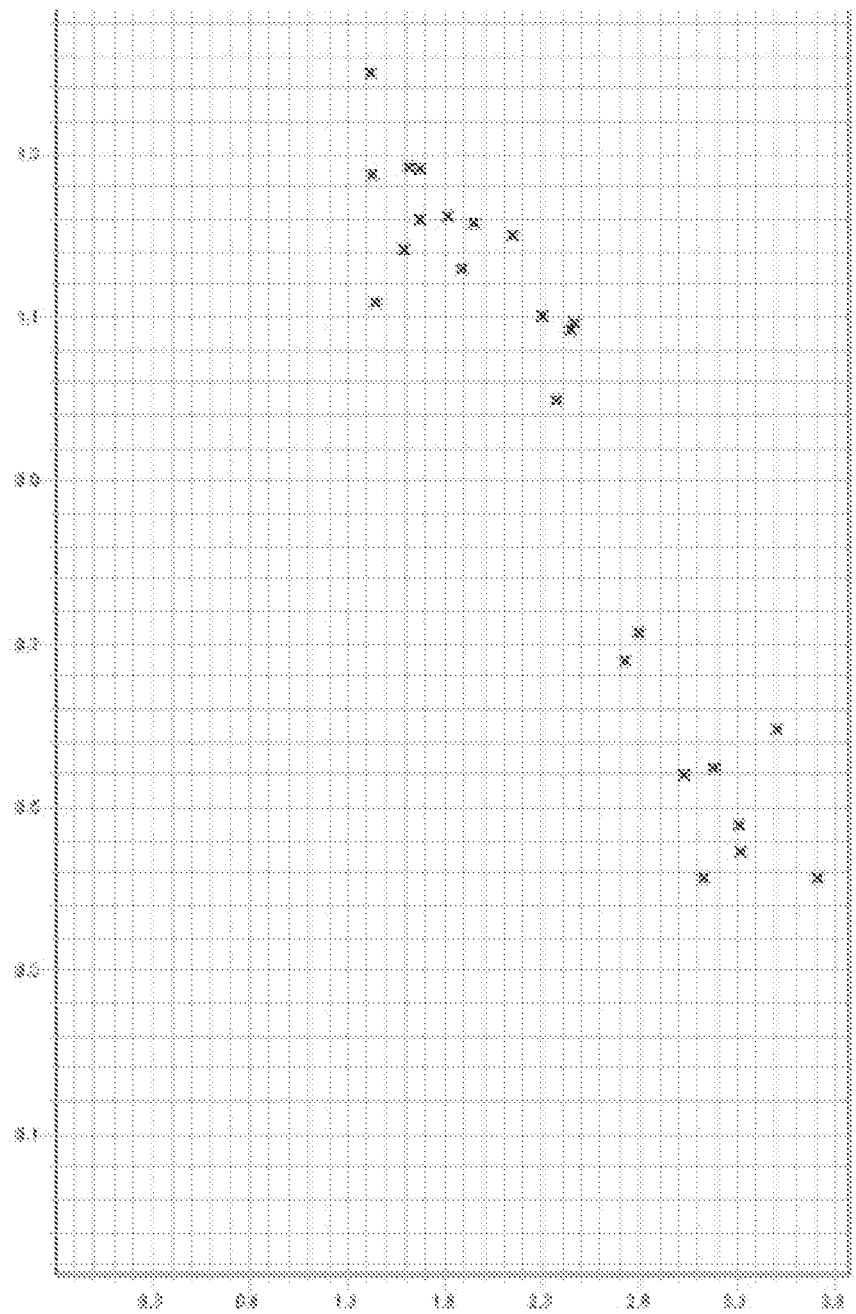

For molecular marker analysis, the DNA from 24 embryos which was released into the soaking solution was used directly as a template for Taqman PCRs. Modification of the DNA (e.g. additional cleaning steps via alcohol precipitation) could be applied. Direct PCR results are shown in FIG. 4.

Example 2

Experiments 5-9

As in example 1 different washing methods post embryo extraction and/or before DNA isolation to remove endosperm tissue and/or DNA of non-embryonic origin were tested. DNA isolation was performed as described in example 1, but germination tests were done in solid medium containing MS buffer and 3% sucrose. Tab.1 summarizes germination results for each experiment of example 2 plus control embryos.

Figure 5:
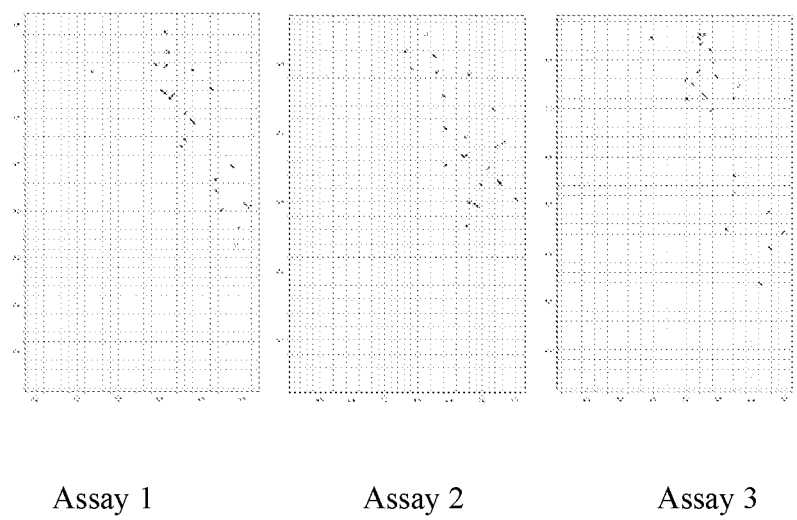

Experiment 5: 24 Embryos were extracted as described above. No post embryo extraction and/or pre DNA isolation washing step was performed. DNA isolation was done as in experiment 1. For molecular marker analysis, the DNA from 24 embryos which was released into the soaking solution was used directly as a template for Taqman PCRs. Modification of the 10 DNA (e.g. additional cleaning steps via alcohol precipitation) could be applied. Direct PCR results for 3 different genotyping Taqman assays are shown in FIG. 5. This figure illustrates how a contamination of paternal DNA can affect the results of marker analysis: Samples for marker 3 are separated into two distinct allelic clusters. No allelic clusters are formed for assay 2, cluster formation for assay 1 is poor. The effect of paternal DNA contamination depends on the paternal allele, a negative affect is only seen if the paternal allele is different from the maternal allele. The effect might also depend on the detection sensitivity for of each assay.

Figure 6:
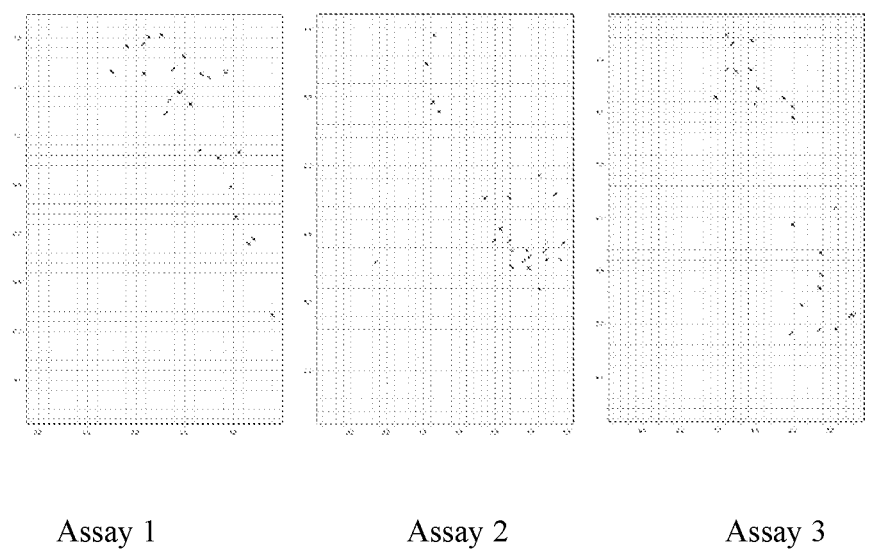

Experiment 6: For the removal of adherent endosperm tissue, 24 embryos were pooled and transferred into a 50 ml tube containing 40 ml $H_2O$. To enhance the washing efficiency, the tube was placed on a horizontal shaker and vigorously shaken for 25 minutes. After 25 minutes the washing solution was poured off and the embryos were briefly rinsed in $H_2O$. DNA extraction and germination test were performed as described under experiment 1. Direct PCR results for the same 3 different assays shown in FIG. 5 are shown in FIG. 6. As seen in experiment 5, not all 3 tested assays show distinct allelic clusters, but assay 2 performing better in experiment 6 than in experiment 5.

Figure 7:
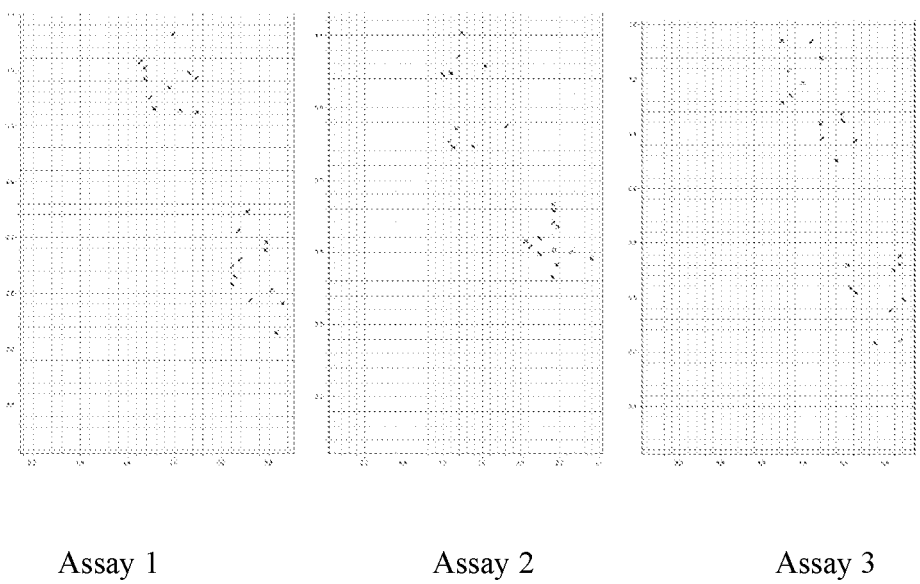

Experiment 7: For the removal of adherent endosperm tissue, 24 embryos were pooled and transferred into a 50 ml tube containing 40 ml MS buffer and 3% sucrose. To enhance the washing efficiency, the tube was placed on a horizontal shaker and vigorously shaken for 25 minutes. After 25 minutes the washing solution was poured off and the embryos were briefly rinsed in $H_2O$. DNA extraction and germination test were performed as described under experiment 1. Direct PCR results for the same 3 different genotyping Taqman assays shown in FIGS. 5 and 6 are shown in FIG. 7. Distinct clusters are formed for all 3 tested assays. Samples of some allelic cluster (assays 2 and 3) are not very tight.

Figure 8:
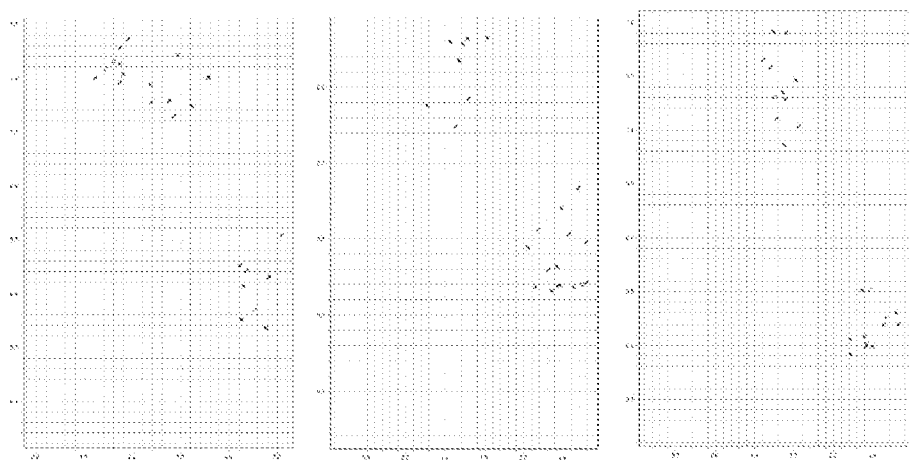

Experiment 8: For the removal of adherent endosperm tissue, 24 embryos were pooled and transferred into a 50 ml tube containing 8% (vol.) silica gel powder (Sigma 288594) in $H_2O$ (total volume: 40 ml). To enhance the washing efficiency, the tube was placed on a horizontal shaker and vigorously shaken for 25 minutes. After 25 minutes the washing solution was poured off and the embryos were briefly rinsed in $H_2O$. DNA extraction and germination test were performed as described under experiment 1. Direct PCR results for 3 different genotyping Taqman assays shown in experiments 5-7 are shown in FIG. 8. The addition of silica powder in the washing solution improved the washing efficiency compared to washing embryos with $H_2O$ only (experiment 6) as seen in example 1 experiment 2.

Figure 9:
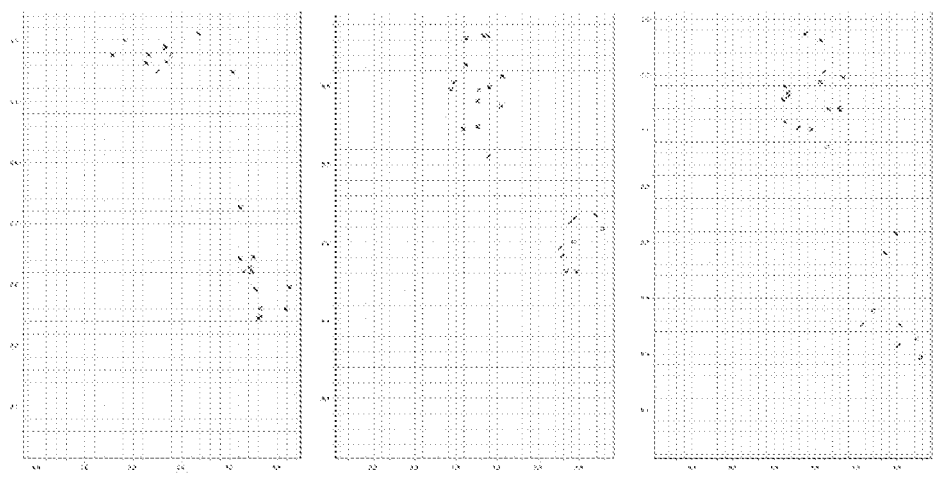

Experiment 9: For the removal of adherent endosperm tissue, 24 embryos were pooled and transferred into a 50 ml tube containing 8% (vol.) silica gel powder (Sigma 288594) in MS with 3% sucrose (total volume: 40 ml). To enhance the washing efficiency, the tube was placed on a horizontal shaker and vigorously shaken for 25 minutes. After 25 minutes the washing solution was poured off and the embryos were briefly rinsed in $H_2O$. DNA extraction and germination test were performed as described under experiment 1. Direct PCR results for 3 different genotyping Taqman assays shown in experiments 5-8 are shown in FIG. 9. As seen in experiments 2 and 6, the addition of silica powder improved the washing efficiency compared to washing the embryos in MS buffer only, resulting in tighter allelic clusters for all tested assays.

TABLE 1

Seedling formation 7 days post DNA extraction.

| Experiment | Initial Number of Immature Corn Haploid Embryos | Number of Seedlings | Percent Germination |
|---|---|---|---|
| Control | 30 | 29 | 97 |
| 5 | 25 | 24 | 96 |
| 6 | 24 | 24 | 100 |
| 7 | 24 | 22 | 92 |
| 8 | 24 | 24 | 100 |
| 9 | 24 | 23 | 96 |

Example 3

Experiments 10-12

Embryos were extracted as described above. Post extraction embryos were not rinsed before placing them onto filter paper containing MS buffer with 3% sucrose. Several methods to remove endosperm tissues were tested (experiments 10-13).

Figure 10:
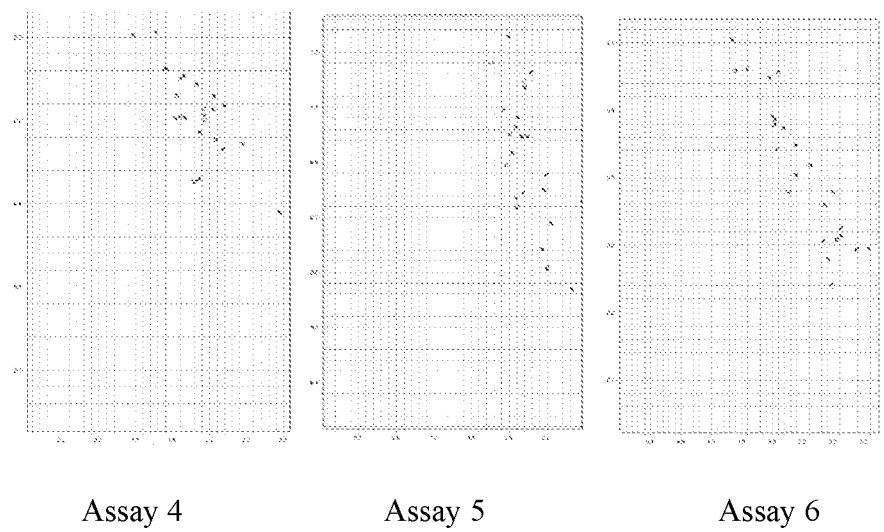

Experiment 10: Embryos which were not rinsed post extraction were placed into wells of 96 well blocks for DNA extraction and an extraction solution added as described above. After one hour isolated DNA was removed, embryos were briefly rinsed in MS buffer containing 3% sucrose and transferred to filter paper containing MS buffer and 3% sucrose to test germination rate. Germination was comparable to untreated controls. Direct PCR results for 3 different genotyping Taqman assays using isolated DNA are shown in FIG. 10. No distinct allelic clusters are formed for the three tested assays due to the presence of various amounts of second alleles. The source of contamination is very likely reminiscent endosperm tissue.

Figure 11:
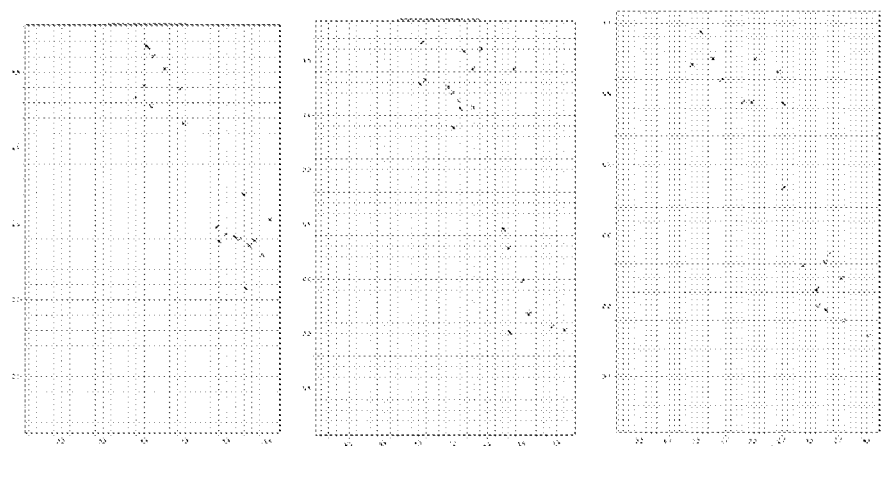

Experiment 11: Embryos were pooled and transferred into a 50 ml tube containing 40 ml MS buffer and 3% sucrose. The tube was placed on a horizontal shaker and vigorously shaken for 25 minutes. After 25 minutes the washing solution was poured off and the embryos were briefly rinsed in $H_2O$ for DNA extraction as described above. After DNA extraction embryos were briefly rinsed with MS buffer containing 3% sucrose and placed into petri dished containing filter paper soaked in MS buffer containing 3% sucrose. Germination was comparable to untreated controls. Direct PCR results for the same 3 genotyping Taqman assays which were used for experiment 10 are shown in FIG. 11. The 25 minutes wash in MS buffer must have removed most of the contaminating endosperm tissue. Distinct allelic clusters are formed for the 3 assays tested.

Experiment 12: As in experiment 11 embryos were not washed before DNA extraction. To enhance DNA yield from embryonic tissue cells were mechanically opened by removing some scutellum tissue with a razor blade. The removed tissue was discarded and the manipulated embryos were placed into wells of 96 well blocks for DNA extraction and an extraction solution added as described in experiment 10. After one hour isolated DNA was removed, embryos were briefly rinsed in MS buffer containing 3% sucrose and transferred to filter paper containing MS buffer and 3% sucrose to test germination rate. Germination was comparable to untreated controls Direct PCR results for the same 3 genotyping Taqman assays which were used for experiment 10 are shown in FIGS. 10 and 11. Distinct allelic clusters are formed, clusters are tighter than seen in experiment 11. This can be due to the fact that more embryonic DNA from mechanically manipulated embryos was obtained than from embryos which were not mechanically manipulated.

Figure 13:
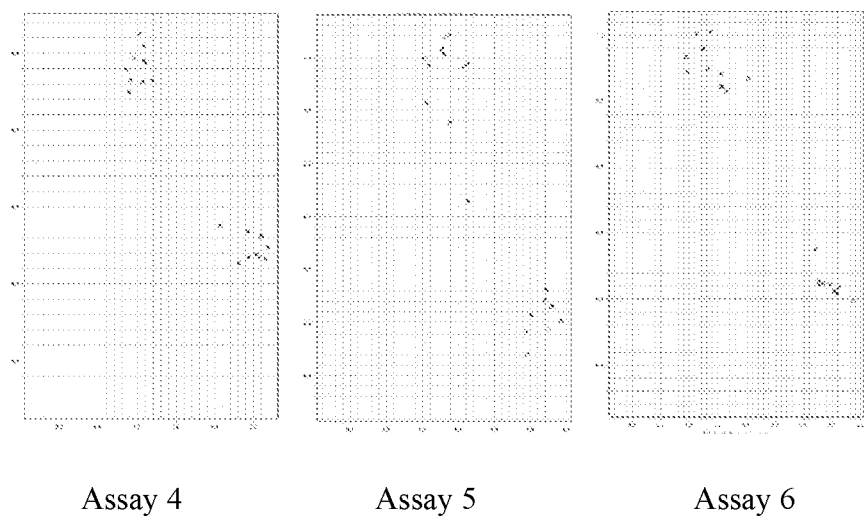

Experiment 13: As in experiment 11 embryos were pooled and transferred into a 50 ml tube containing 40 ml MS buffer and 3% sucrose. The tube was placed on a horizontal shaker and vigorously shaken for 25 minutes. After 25 minutes the washing solution was poured off. As in experiment 12 some scutellum tissue from each embryo was removed with a razor blade. The removed tissue was discarded. To enhance DNA yield from embryonic tissue cells were mechanically opened by removing some scutellum tissue with a razor blade as in experiment 12. The removed tissue was discarded and the manipulated embryos were placed into wells of 96 well blocks for DNA extraction and an extraction solution added as described in experiment 1. After one hour isolated DNA was removed, embryos were briefly rinsed in MS buffer containing 3% sucrose and transferred to filter paper containing MS buffer and 3% sucrose to test germination rate. Germination was comparable to untreated controls Direct PCR results for the same 3 genotyping Taqman assays which were used for experiment 10 are shown in FIG. 13. Distinct allelic clusters are formed, clusters are tighter than seen in experiment 11-12. As in experiment 12 this can be due to the fact that more embryonic DNA from mechanically manipulated embryos was obtained than from embryos which were not mechanically manipulated.

FIGURES

The allelic discrimination plots in FIGS. 1 to 13 have X-axis labels Allele X (Robot Test 1) and Y-axis labels Allele Y (Robot Test Y).

FIG. 1. Allele identification from individual haploid corn embryos not rinsed post embryo isolation but washed in MS buffer containing sucrose before DNA extraction.

FIG. 2. Allele identification from individual haploid corn embryos not rinsed post embryo isolation but washed in MS buffer containing sucrose and silica powder before DNA extraction.

FIG. 3. Allele identification from individual haploid corn embryos rinsed post embryo isolation and washed in MS buffer containing sucrose before DNA extraction.

FIG. 4. Allele identification from individual haploid corn embryos rinsed post embryo isolation and washed in MS buffer containing sucrose and silica powder before DNA extraction.

FIG. 5 Allelic plots for 3 assays. No embryo washing step before DNA extraction.

FIG. 6: Allelic discrimination plots for 3 assays. Embryos washed in $H_2O$ before DNA extraction.

FIG. 7: Allelic discrimination plots for 3 assays. Embryos washed in MS buffer containing 3% sucrose before DNA extraction.

FIG. 8: Allelic discrimination plots for 3 assays. Embryos washed in $H_2O$ containing silica powder before DNA extraction.

FIG. 9: Allelic discrimination plots for 3 assays. Embryos washed in MS buffer/3% sucrose containing silica powder before DNA extraction.

FIG. 10: Allelic discrimination plots for 3 assays. Embryos were not rinsed post extraction. No washes were performed before DNA extraction.

FIG. 11: Allelic discrimination plots for 3 assays. Embryos were not rinsed post extraction but washed with MS buffer containing 3% sucrose.

Figure 12:
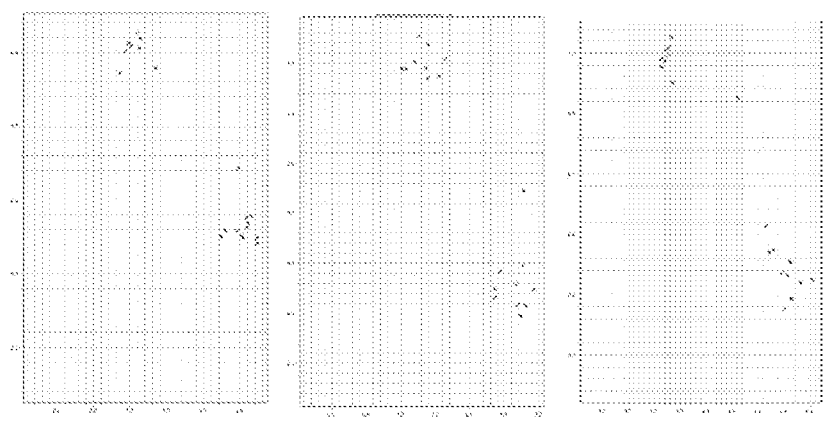

FIG. 12: Allelic discrimination plots for 3 assays. Embryos were not rinsed post extraction. No washes were performed Some scutellum tissue was removed with a razor blade and discarded before soaking embryos in cell lysis solution.

FIG. 13: Allelic discrimination plots for 3 assays. Embryos were not rinsed post extraction but washed with MS buffer containing 3% sucrose. Some scutellum tissue was removed with a razor blade and discarded before soaking embryos in cell lysis solution.

The invention claimed is:

1. A viability-retaining method of selecting corn embryos having a desired trait, said method comprising:
   a) extracting embryos;
   b) removing associated non-embryogenic tissue or DNA from the exterior of the embryo; and
   c) extracting DNA directly from the embryo by contacting the embryos with a cell lysis solution which disrupts cells but does not reduce embryo viability.

2. The method according to claim 1, wherein steps a) and b) are performed simultaneously using a liquid stream of solution.

3. The method according to claim 1, wherein step b) comprises contacting the embryos with a solution comprising nutritional salt and optionally a carbohydrate source before DNA extraction.

4. The method according to claim 1, wherein step c) comprises contacting the embryos with a soaking solution comprising nutritional salt and optionally a carbohydrate source after DNA extraction.

5. The method according to claim 1, wherein step b) comprises contacting the embryos with a solution comprising a nutritional salt and optionally a carbohydrate source before DNA extraction and step c) comprises contacting the embryos with a soaking solution comprising a nutritional salt and optionally a carbohydrate source after DNA extraction.

6. The method according to claim 1, wherein step b) comprises washing the embryos post extraction to remove associated non-embryogenic tissue or DNA before DNA extraction directly from the embryo.

7. The method according to claim 6, wherein the washing step comprises contacting the embryos with a liquid.

8. The method according to claim 6, wherein the washing step further comprises the use of an abrasive.

9. The method according to claim 1, wherein the embryos are mechanically opened to further facilitate removal of DNA from ruptured embryonic cells.

10. The method according to claim 1, wherein step b) further comprises removing contaminants enzymatically.

11. The method according to claim 1, wherein molecular marker analysis is performed using DNA extracted from embryos.

12. The method according to claim 11, wherein the DNA is additionally cleaned or concentrated via alcohol precipitation.

13. The method according to claim 1, wherein the embryo is an immature embryo.

14. The method according to claim 1, wherein the method is automated or semi-automated.

\* \* \* \* \*